United States Patent [19]
Jacobs et al.

[11] Patent Number: 4,978,007
[45] Date of Patent: Dec. 18, 1990

[54] PACKAGING CURABLE MATERIALS

[75] Inventors: Dwight W. Jacobs, River Falls, Wis.; Gregory D. Crowe, Duarte, Calif.

[73] Assignee: Minnesota Mining and Manufacturing Company, St. Paul, Minn.

[21] Appl. No.: 350,609

[22] Filed: May 10, 1989

[51] Int. Cl.$^5$ ............................................. B65D 83/10
[52] U.S. Cl. ..................... 206/469; 206/368; 206/460; 206/813
[58] Field of Search ............... 206/813, 800, 368, 369, 206/460

[56] References Cited

U.S. PATENT DOCUMENTS

| | | | |
|---|---|---|---|
| 3,212,913 | 10/1965 | MacKenzie | 206/813 |
| 3,265,202 | 8/1986 | Cornell | |
| 3,509,991 | 5/1970 | Hurst | 206/813 |
| 3,692,469 | 9/1972 | Peace | 206/813 |
| 3,797,115 | 3/1974 | Silverman et al. | |
| 4,078,662 | 3/1978 | Volland | 206/800 |
| 4,094,068 | 6/1978 | Schinhammer | |
| 4,117,596 | 6/1978 | Wallshein | |
| 4,204,325 | 5/1980 | Kaelble | |
| 4,251,712 | 2/1981 | Park | 206/813 |
| 4,489,487 | 12/1984 | Bura | 206/813 |

OTHER PUBLICATIONS

Richard F. Ceen, "Orthodontic Bonding-An Overview", *The Journal of Pedodontic*, Fall 1980, pp. 62–71.

*Primary Examiner*—Joseph Man-Fu Moy
*Attorney, Agent, or Firm*—Wegner, Cantor, Mueller & Player

[57] ABSTRACT

Disclosed is a packaged element containing (a) a substrate that transmits less than about 0.5% of actinic radiation and has at least one recess, (b) a cover that transmits less than about 0.5% of actinic radiation and transmits at least part of the visible light spectrum, (c) a structure for maintaining the cover in contact with the substrate such that the cover filters incident radiation entering the recess, and (d) an element located in the recess and having a substance thereon that is curable by exposure to the actinic radiation. Also disclosed is an article containing (a) a substrate having at least one recess with an interior surface, (b) an element having a tacky substance on a surface thereof, and (c) a structure for positioning the element inside the recess such that the tacky substance does not separate from the element upon removal from the recess.

31 Claims, 4 Drawing Sheets

PACKAGING CURABLE MATERIALS

The present invention relates to packaging an element having a curable material coated thereon. In particular it relates to such a packaging wherein the materials are light-reactive, tacky, or both, and the element is an orthodontic bracket.

Orthodontic brackets are typically packaged in bulk or in single-patient trays. Orthodontic brackets having a layer of unactivated adhesive material covered with a protective liner are disclosed in U.S. Pat. No. 4,205,325.

The present invention provides a packaged element comprising (a) a substrate that transmits less than about 0.5% of selective actinic radiation and has at least one recess, (b) a cover that transmits less than about 0.5% of the actinic radiation and transmits at least part of the visible light spectrum, (c) a means for maintaining the cover in contact with the substrate such that the cover filters incident radiation entering the recess, and (d) an element located in the recess and having a substance thereon that is curable by exposure to the actinic radiation. The present invention also provides an article comprising (a) a substrate having at least one recess with an interior surface, (b) an element having a tacky substance thereon, and (c) a means for positioning the element inside the recess such that the tacky substance does not separate from the element upon removal from the recess.

Figure 7:
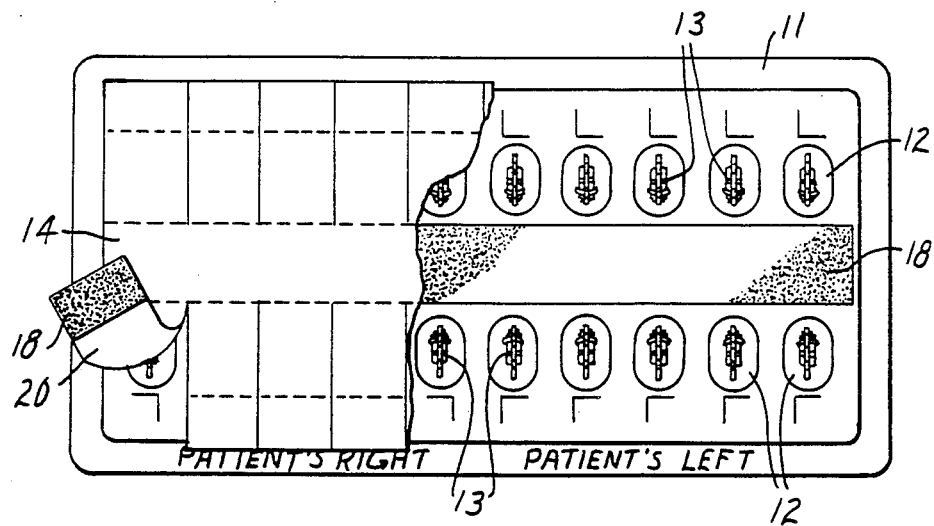
FIG. 7 is a top view.
Figure 8:
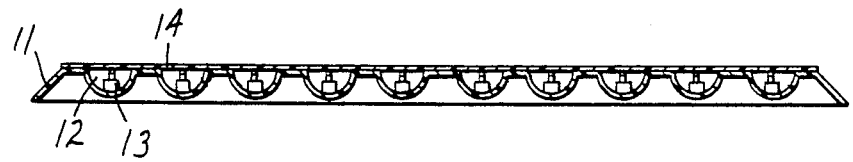
FIGS. 8 and 9 are side views of a preferred embodiment of the present invention.
Figure 9:
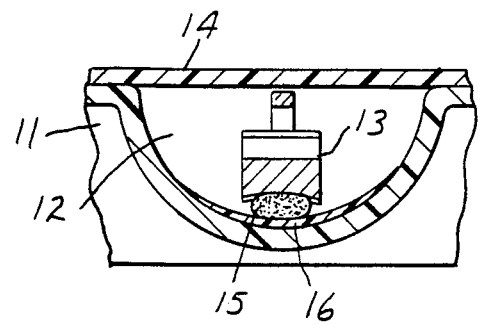

In one embodiment of the present invention, a tray containing orthodontic brackets pre-coated with adhesive paste and placed into release-layer-coated recesses (wells) is provided. The adhesive paste is curable upon exposure to selective actinic radiation, i.e., wavelengths of light (electromagnetic radiation) that effect curing in a particular material. Referring to FIGS. 7, 8, and 9, the embodiment contains a tray 11, such as a vacuum-formed 6.35 × 15.24 cm tray made from a black (opaque) semi-rigid 0.508–0.635 mm thick high-impact polystyrene sheet. The tray includes wells 12, each of which has a concave inner surface deep enough to accommodate a standard orthodontic bracket 13, which is coated with light-curable adhesive paste 15, completely below the rim of the well. The bottom of each well is coated with an excess (0.3–0.4 grams) of a non-adhesive release-coating material 16, e.g., a silicone, polyethylene, or fluoropolymer coating such as those commercially available under the names Teflon TM poly-tetrafluoroethylene and Teflon TM fluorinated ethylene-propylene (available from E.I. du Pont de Nemours, Wilmington, Del.) and Silicone Premium (a siloxane available from General Electric Company, Waterford, N. Y.). A blue-light-filtering film 14 covers the wells and is secured to the tray with double-sided, repositionable pressure-sensitive adhesive tape 18. The cover 14 is cut to form individual flaps 20, which allow access to individual wells as shown in FIG. 7. Each flap 20 has a piece of double-sided, repositionable pressure-sensitive adhesive tape 18, which maintains the flap in contact with the tray. Alternatively, access to the brackets can be provided via a star-burst pattern of slits cut into the film above each well. Preferably, the film is a flexible, colored transparent film, opaque to the wavelength of light required to cure the paste, but sufficiently transparent to non-curing wavelengths to permit viewing the bracket through the film.

Figure 10:
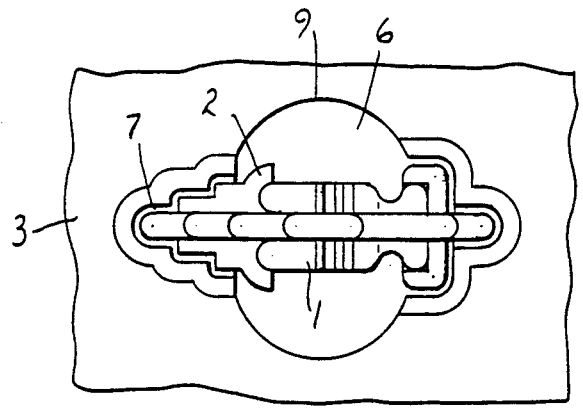
FIG. 10 is a top view.
Figure 11:
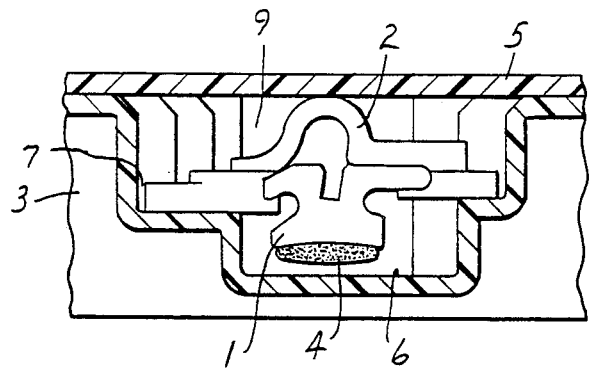
FIG. 11 is a cross-sectional view of another preferred embodiment of the present invention.

In another embodiment of the present invention, orthodontic brackets coated with a light-curable adhesive paste are provided in a tray in which each bracket is suspended in a recess designed to keep the adhesive paste from contacting the surface of the recess. As shown in FIGS. 10 and 11, bracket 1 is attached to a conventional long-axis indicator 2, the ends of which, by virtue of cooperation with complimentally-shaped, linearly-aligned grooves 7 on opposing sides of well 9 in tray 3, suspend the bracket above the bottom 6 of well 9 such that adhesive paste 4 on bracket 1 does not contact any part of the tray. Cover film 5 (not seen in FIG. 10) is attached to the tray 3 by a double-sided, repositionable, pressure-sensitive adhesive tape (not shown) sandwiched between the film and the tray. As demonstrated in the figures, groove 7 and long-axis indicator 2 are shaped to engage in such a way that the indicator rests loosely in the groove while preventing lateral or rotational movement of the bracket 1 within the well 9. Cover film 5 contacts the top of the long-axis indicator 2 to hold the indicator in the groove 7. In this manner, cover film 5 and groove 7 cooperate with the long-axis indicator 2 to fix the bracket 1 loosely in the well 9.

Figure 1:
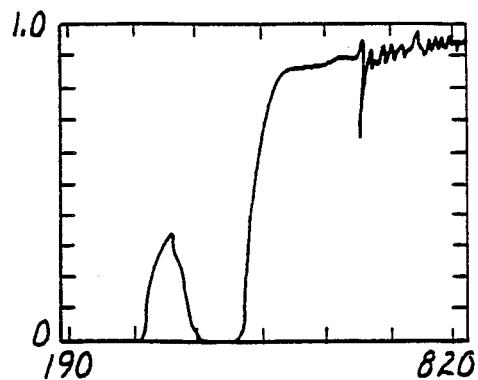
FIGS. 1–6 are curves showing % transmittance vs. wavelength (determined using a Hewlett-Packard HP 8451A Diode Array Spectrophotometer) for various dyes useful in accordance with the present invention.
Figure 4:
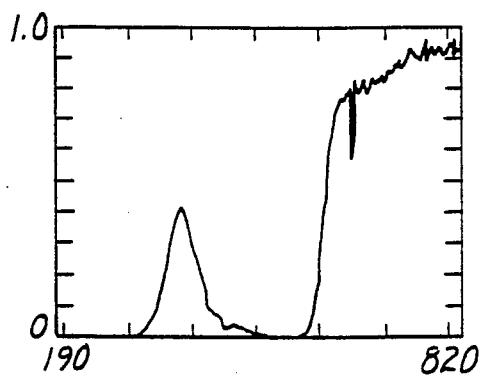
Figure 2:
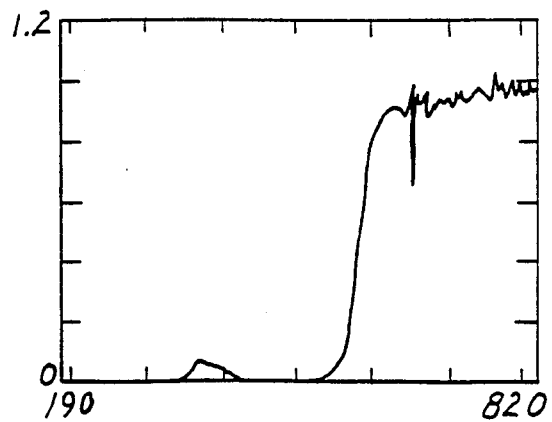
Figure 3:
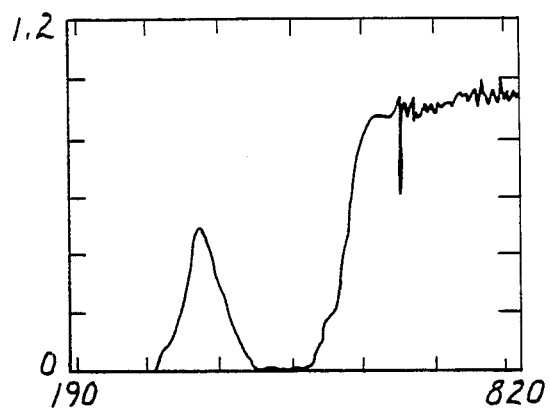
Figure 5:
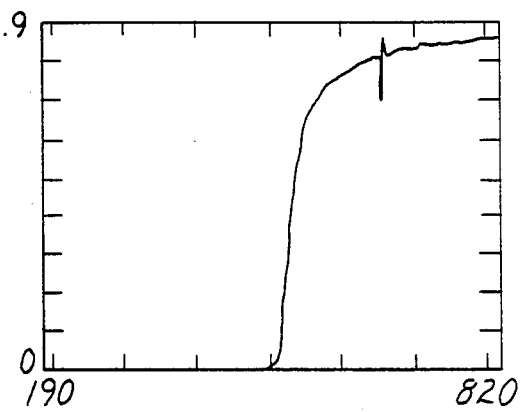
Figure 6:
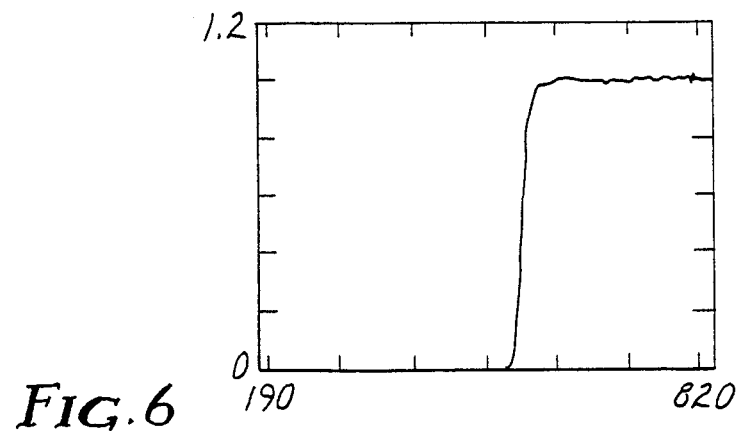

In accordance with the present invention various materials are useful for the cover and substrate. Commercially available flexible films that are useful as the cover in accordance with the present invention include, e.g., polyester materials available from Rosco Labs, Inc., Port Chester, N.Y. under the name Roscolux TM 12 (38.1 μm thick, straw color, % transmittance curve for electromagnetic radiation shown in FIG. 1), Roscolux TM 22 (99 μm thick, deep-amber color, % transmittance curves for electromagnetic radiation shown in FIG. 2), Roscolux TM 23 (38.1 μm thick, orange color, % transmittance curves for electromagnetic radiation shown in FIG. 3), Roscolux TM 42 (38.1 μm thick, deep-salmon color, % transmittance curves for electromagnetic radiation shown in FIG. 4), and vinyl materials, such as a 0.343 mm thick film having % transmittance curves for electromagnetic radiation as shown in FIG. 5 (available from Frommelt Industries, Inc. Dubuque, Iowa, under the designation Saf-T-Vu yellow, M1063). Flexible films useful as covers in accordance with the present invention have a preferable thickness between about 0.00254 and 2.54 mm, more preferably between about 0.0254 and 0.254 mm. Alternatively, rigid sheets instead of flexible films can be used, which are attached to the tray so as to permit access to the individual brackets, e.g., such as by a hinge or by cooperating tongue-and-groove appendages that permit the plate to slide relative to the tray. Useful rigid sheets include, e.g., a poly(methyl methacrylate) acrylic material having % transmittance curves as shown in FIG. 6, which has a thickness of about 3.05 mm (available from Rohm & Haas, Philadelphia, Penna. under the designation Amber 2422). Other useful covers include polymeric materials, e.g., polyesters such as poly(cyclohexane-1,4-dimethylene terephthalate), poly(ethylene terephthalate), and poly(butylene terephthalate), polycarbonates such as poly(4,4'-isopropyl-diphenyl carbonate), poly(vinyl chloride), and polypropylene. Useful rigid materials include, e.g., poly(methyl methacrylate), polyethylene, and polystyrene. Other useful cover materials include acrylic polymers, polycarbonates, polyolefins, fluorocarbon polymers, and inorganic glasses.

Various colorants (i.e., pigments, and/or dyes) are useful for making the cover absorb selective wavelengths of electromagnetic radiation. Colorants can be incorporated into both rigid sheets and flexible films according to well known methods, e.g., as disclosed in the *Modern Plastics Encyclopedia* Vol. 65, No. 11, pp. 148–150, McGraw-Hill, New York (1988). Generally, this involves blending the colorant with a molten resin and then forming the product into pellets. These pellets are then used as feed, e.g., in extruding films of desired thicknesses. The amount of colorant necessary per unit of resin to provide the desired protection will vary depending upon various factors, such as the particular colorant used, thickness of the resulting film or sheet, wavelength of light to be absorbed, and the capacity of the non-colorant-treated material to absorb light of the wavelength to be filtered. Preferably, the amount of colorant used is sufficient to enable the cover to absorb at least about 80%, preferably about 95–100%, of selective actinic radiation, i.e., light in the wavelength range useful in curing the packaged material. Alternatively, the colorant can be coated onto the cover after it has been formed.

The particular colorant necessary to absorb actinic radiation from a selected range of the electromagnetic spectrum can be readily determined by the skilled artisan. Various commercially available colorants known by their color index (C.I.) identification (See *Colour Index Third Edition*, The Society of Dyers and Colourists, England, 1971) absorb (i.e., do not freely transmit) different wavelengths of the electromagnetic spectrum. For example, C.I. Disperse Yellow 201 (available from Mobay Corporation, New Jersey under the name Macrolex Yellow 6G), a styryl dye that absorbs wavelengths between about 415 and 480 nm; C.I. Solvent Blue 97 (available from Mobay Corporation under the name Macrolex Blue RR), an anthraquinone dye that absorbs wavelengths between about 550 and 650 nm; C.I. Solvent Red 135 (available from Mobay Corporation under the name Macrolex Red EG), a perinone dye that absorbs wavelengths between about 440 and 570 nm; C.I. Solvent Orange 60 (available from Mobay Corporation under the name Macrolex Orange 3G), a perinone dye that absorbs wavelengths between about 380 and 515 nm; and C.I. Solvent Yellow 14 (available from Mobay Corporation under the name Ceres Orange RA), a monoazo dye that absorbs wavelengths between about 350 and 530 nm. Dyes that absorb wavelengths in the ultraviolet range (i.e., about 300–390 nm), but which impart very little color, e.g., hydroxyphenyl benzotriazoles, such as 2-(2'-hydroxy-5'-methylphenyl)benzotriazole and 2-(3',5'-di-tert-butyl-2'-hydroxyphenyl)-5-chlorobenzotriazole, and benzophenones, such as 2,4-dihydroxybenzophenone, 2-hydroxy-4-methoxybenzophenone, and 2,2'-dihydroxy-4,4'-dimethoxybenzophenone, are also commercially available, e.g., dyes available from Ciba-Geigy Corporation, New York, under the names Tinuvin ™ - P, -324, -326, -327, and -328 and dyes available from BASF Wyandotte Corporation, New Jersey, under the names Uvinul ™ -400, M-40, and D-49. The cover preferably transmits visible light outside the range of the actinic radiation that will cure the light-curable material. This allows the practitioner to see the material-coated element through the cover while retaining the light-curable material in an un-cured state. However, the cover can be opaque as well.

Various substrate materials useful in accordance with the present invention include, e.g., plastics such as poly(acrylonitrile-butadiene-styrene) copolymers (ABS polymers), poly(vinyl chloride) (PVC), poly(methyl methacrylate) (PMMA), polyethylene (PE), polystyrene (PS), and polypropylene (PP); metals, e.g., carbon steel, 303 stainless steel, and 316 stainless steel; wood, e.g., oak, maple, pine, and walnut; and other durable materials such as ceramics and glasses. In one embodiment, the substrate is an injection-molded, black polypropylene tray. Substrates made from transparent materials, such as many plastics and glasses, are preferably opacified, using pigments such as titanium dioxide and carbon black, or modified with colorants as previously detailed for use in the cover sheet, in order to prevent electromagnetic radiation from reaching the adhesive material packaged therein. The substrate can be designed in various ways in accordance with the present invention, e.g., as shown in the accompanying figures. Other substrate examples based on the specific embodiments presented include, e.g., providing recesses large enough to accommodate more than one element, modifying the contour of the interior surface of the recesses to accommodate different shaped elements, and having projections emanating from the interior surface of the recess from which an article can be suspended. Substrates useful in accordance with the present invention can be made according to known methods, e.g., as disclosed in the aforesaid *Modern Plastics Enclopedia*.

Various means are useful for maintaining the cover in contact with the substrate in accordance with the present invention. Preferably, an adhesive is used, either by itself or as part of a double-sided or single-sided adhesive tape. The adhesive can be an aggressive (permanent) adhesive, e.g., as disclosed in U.S. Pat. Nos. 3,691,140, 3,873,638 3,922,464, 4,379,883, 4,413,080, 4,599,265, or RE 24906, the disclosures of which are incorporated herein by reference. Alternatively, the adhesive can be a pressure-sensitive, repositionable adhesive, e.g., as disclosed in U.S. Pat. Nos. 3,620,988, 3,691,140, 3,857,731, 4,166,152, 4,587,152, 4,645,783, 4,656,218, 4,735,837, and 4,786,696, the disclosures of which are incorporated herein by reference. In addition to adhesive means, other useful means include a hinge-and-clasp fastening arrangement, which permits lifting the cover to permit removal of a bracket and then lowering and fastening the cover to the substrate to protect the remaining brackets, or a tongue-and-groove arrangement, which permits sliding of the cover with respect to the substrate. The cover can also be heat-sealed to the substrate. Additionally, the cover can be in one piece covering all of the recesses in the substrate, or in several pieces, either completely separate or partially connected, each piece covering one or more substrate recesses.

The present invention is useful for packaging a variety of elements in accordance with the present invention, e.g., adhesive-coated orthodontic brackets as discussed above. Useful adhesive-coated orthodontic brackets include, e.g., those disclosed in U.S. Pat. No. 4,204,325 and European Pat. Application No. 0 290 133, the disclosures of which are incorporated herein by reference. Other useful elements containing radiation-curable materials, tacky materials, or both will be apparent to the skilled artisan.

What is claimed is:

1. A packaged element comprising:
   (a) a substrate that transmits less than about 0.5% of selective actinic radiation and having at least one recess,
   (b) a cover that transmits less than about 0.5% of the actinic radiation and transmits at least part of the visible light spectrum,
   (c) means for maintaining the cover in contact with the substrate such that the cover filters incident radiation entering the recess, and
   (d) an element located in the recess and having a substance thereon that is curable by exposure to the actinic radiation.

2. The packaged element of claim 1 wherein the actinic radiation has a wavelength in the visible range.

3. The packaged element of claim 1 wherein the actinic radiation has a wavelength between about 300 and 800 nm.

4. The packaged element of claim 1 wherein the actinic radiation has a wavelength between about 400 and 500 nm.

5. The packaged element of claim 1 wherein the substrate comprises an opaque rigid tray.

6. The packaged element of claim 1 wherein the cover comprises a flexible, polymeric film.

7. The packaged element of claim 1 wherein the means maintains the cover in releasable contact with the substrate.

8. The packaged element of claim 1 wherein the means comprises a pressure-sensitive adhesive sandwiched between the cover and the surface of the substrate.

9. The packaged element of claim 1 wherein the substrate has more than one recess.

10. The packaged element of claim 9 wherein the cover has individual flaps, each of which covers a recess and is movable to permit access to the recess it covers.

11. An article comprising:
    (a) a substrate with at least one recess with an interior surface,
    (b) an orthodontic bracket having a tacky substance on an exterior surface thereof, and
    (c) a release coating, sandwiched between the tacky substance and the interior surface of the recess, for positioning the bracket inside the recess such that the tacky substance does not separate from the bracket upon removal of the bracket from the recess.

12. The article of claim 11 wherein the tacky substance is a paste that is curable upon exposure to selective actinic radiation.

13. The article of claim 12 wherein the substrate transmits less than about 0.5% of the actinic radiation and the article further comprises:
    (d) a cover that transmits less than about 0.5% of the actinic radiation, and
    (e) a means for maintaining the cover in contact with the substrate such that the cover filters incident radiation entering the recess.

14. The article of claim 13 wherein the means for maintaining the cover maintains the cover in releasable contact with the substrate.

15. The article of claim 13 wherein the cover transmits at least part of the visible light spectrum.

16. The article of claim 11 wherein the bracket is suspended in the recess such that the tacky substance does not contact the interior surface of the recess.

17. The article of claim 11 which further comprises a seat in the recess that receives the bracket while restricting the tacky substance from contacting the interior surface of the recess.

18. The article of claim 17 wherein the seat comprises linearly-aligned groves on opposing sides of the recess.

19. The article of claim 17 wherein the tacky substance comprises a paste that is curable upon exposure to selective actinic radiation.

20. The article of claim 19 wherein the substrate transmits less than about 0.5% of the actinic radiation and the article further comprises:
    (d) a cover that transmits less than about 0.5% of the actinic radiation, and
    (e) a means for maintaining the cover in contact with the substrate such that the cover filters incident radiation entering the recess.

21. The article of claim 20 wherein the cover transmits at least part of the visible light spectrum.

22. The article of claim 20 wherein the means maintains the cover in releasable contact with the substrate.

23. The article of claim 20 wherein the bracket further comprises a member that rests in the seat and is removably attached to the bracket.

24. The article of claim 20 wherein the seat and cover cooperate to loosely fix the bracket in the recess.

25. The article of claim 11 wherein the tacky substance is a paste that is curable upon exposure to selective actinic radiation.

26. The article of claim 25 wherein the substrate transmits less than about 0.5% of the actinic radiation and the article further comprises:
    (d) a cover that transmits less than about 0.5% of the actinic radiation, and
    (e) a means for maintaining the cover in contact with the substrate such that the cover filters incident radiation entering the recess.

27. The article of claim 26 wherein the cover transmits at least part of the visible light spectrum.

28. The article of claim 26 wherein the means maintains the cover in releasable contact with the substrate.

29. The article of claim 26 wherein the substrate has more than one recess and wherein the cover has individual flaps, each of which covers a recess and is movable to permit access to the recess it covers.

30. The article of claim 26 wherein the cover has slits that permit access to the recess.

* * * * *